US006881878B2

(12) United States Patent
Gutteridge et al.

(10) Patent No.: US 6,881,878 B2
(45) Date of Patent: Apr. 19, 2005

(54) PLANT GENES ENCODING PANTOTHENATE SYNTHETASE

(75) Inventors: Steven Gutteridge, Wilmington, DE (US); Leslie T. Harvell, Newark, DE (US); Emil M. Orozco, Jr., West Grove, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 145 days.

(21) Appl. No.: 10/033,269

(22) Filed: Nov. 13, 2001

(65) Prior Publication Data

US 2003/0167503 A1 Sep. 4, 2003

Related U.S. Application Data

(60) Provisional application No. 60/247,938, filed on Nov. 13, 2000.

(51) Int. Cl.[7] .......................... A01H 1/00; C07H 21/04; C07K 14/415; C12N 5/14; C12N 9/00
(52) U.S. Cl. ...................... 800/295; 435/6; 435/69.1; 435/468; 435/419; 435/252.3; 435/320.1; 530/370; 536/23.6; 800/278
(58) Field of Search ................. 435/6, 69.1, 468, 435/419, 252.3, 320.1, 70.1, 91.4, 469, 183, 410; 530/370; 536/23.6, 23.2; 800/278, 295

(56) References Cited

FOREIGN PATENT DOCUMENTS

WO     WO 99/42565 A1     8/1999

OTHER PUBLICATIONS

Ulrich Genschel et. al., Biochem. Journal, vol. 341:669–678, 1999, The Final Step of Pantothenate Biosynthesis in Higher Plants: Cloning and Characterization of Pantothenate Synthetase from Lotus Japonicus and Oryza Sativum (Rice).
National Center for Biotechnology Information General Identifier NO: 2292978, Aug. 27, 1999, Genschel, U. et. al., The Final Step of Pantothenate Biosynthesis in Higher Plants: Cloning and Characterization of Pantothenate Synthetase from Lotus Japonicus and Oryza Sativum.
National Center for Biotechnology Information General Identifier NO: 2292921, Aug. 27, 1999, Genschel, U. et al., The Final Step of Pantothenate Synthetase from Lotus Japonicus and Oryza Sativum.
V. Rossi et al., Mol. Gen. Genet., vol. 258:288–296, 1998, Identification and Characterisation of an RPD3 Homologue from Maize (Zea Mays L.) That is able to Complement an RPD3 Null Mutant of Saccharomyces Cerevisiae.
Daniel Gachotte et al., The Plant Journal, vol. 9:391–398, 1996, Isolation and Characterization of an Arabidopsis Thaliana CDNA Encoding A 7–Sterol–C–5–Desaturase By Functional Complementation of a Defective Yeast Mutant.
Sebastian Y. Bednarek et al., Plant Physiol, vol. 104:591–596, 1994, A Small GTP–Binding Protein from Arabidopsis Thaliana Functionally Complements the Yeast YPT6 Null Mutant.

Primary Examiner—Phuong T. Bui

(57) ABSTRACT

This invention relates to isolated nucleic acid fragments encoding pantothenate synthetases. The invention also relates to the construction of chimeric genes encoding all or a portion of the pantothenate synthetases, in sense or antisense orientation, wherein expression of the chimeric genes results in production of altered levels of the pantothenate synthetases in transformed host cells.

11 Claims, 2 Drawing Sheets

Alignment of Pantothenate Synthetases From Corn, Eucalyptus, Soybean, Tulip, Wheat, Rice, and Lotus

```
SEQ ID NO:2      cpj1c.pk005.c12fis    [corn]
SEQ ID NO:4      cr1n.pk0125.c12fis    [corn]
SEQ ID NO:7      eej1c.pk005.p14fis    [eucalyptus]
SEQ ID NO:9      ssl.pk0021.d7fis      [soybean]
SEQ ID NO:11     etb1c.pk004.j20fis    [tulip]
SEQ ID NO:13     wlm96.pk036.k8fis     [wheat]
SEQ ID NO:14     gi2292978             [rice]
SEQ ID NO:15     gi2292921             [lotus]
```

```
                 1                                                                                           90
SEQ ID NO:2      MAAAAAA-------VHEPEVIRDKAAMRAWSRRRRRAEGKAVALVPTMGFLHEGHLSLISAAVAAS-AGPIAVVVSIYNPSQFAPTEDLA
SEQ ID NO:4      MAAAAA--------VHEPEVIRDKAAMRAWSRRRRRAEGKAVALVPTMGFLHEGHLSLSLVSAAVAAS-AGPVAVVVSIYNPSQFAPTEDLA
SEQ ID NO:7      MAAPP---------KEPLVITDKAEMREWSRSARRQGRTIALVPTMGFLHEGHLSLVREARRADA---VVVSVYNPGQFAPSEDLS
SEQ ID NO:9      MAPAP---------R----VISDKASMRSWSRSMRPAQGKLIGLVPTMGFIHAGHLSLIVAQARQLSDV----VAVSIYVNPGQFAPTEDLS
SEQ ID NO:11     MAAAPAASSAAAAASVSEPVIITSKPEMLAWSRHIHRRLSHTIALVPTMGSLHAGHLSLISHAASLADLT----VVSIYLNPTQFAPSEDLA
SEQ ID NO:13     MAAAG---------EPEVIRDKAAMRAWSRRQRAEGKTVVLVPTMGFLHEGHLSLVSAA-AAV-PGPVAVVVSIYVNPSQFAPTEDLA
SEQ ID NO:14     MA--P---------VISDKDEMRKWSRSMRSQGKLIALVPTMGFLHEGHLSLVRDAHNHADL---VAVSIYVNPGQFSPTEDLS
SEQ ID NO:15     MAAP----------REPEVIRDKAAMRAWSRRRRAEGKIVAVVPTMGYLHQGHLSLISAAAAAASADPVAIVVTIYVNPSQFAPSEDLA 91                                                                                          180
SEQ ID NO:2      TYPSDFAGDLRKLAAT-GVVAAVFCPPDLYVRGSA--DRPSAAGASGGAVSCLEDAGGHAHETWIRVERLEKGLCGSSRPVFFRGVATVV
SEQ ID NO:4      TYPSDFAGDLGKLAAT-GVVAAVFCPPDLYVRGSA--DRPSAASASGGAVSCLEDAGGHAHETWIRVERI.EKGLCGSSRPVFFRGVATVV
SEQ ID NO:7      TYPSDFEGDLGKLRAVPGGVDVVFHRPQNLYDYGQREVG-GSGVESDNGSVSCLEEK-GMGHEAWVRVERLEKGMCGKSRPVFFRGVATVV
SEQ ID NO:9      TYPSDFDGDVKKLASVPGGVDVVFHPRNLYDYGKNGGG-DVAEAGG--MVSCVE--SGSGHESWVRVEKLELGLCGKSRPVFFRGVATVV
SEQ ID NO:11     TYPADLAADLRNLRAC-PSVAAVFCPTNPY-------------------ADGHETWVRVEELERGLCGLSRPVFFRGVATVV
SEQ ID NO:13     TYPSDLAGDLRKLAST-GAVHAVFNPPDLYHRGAAVSGRRAEAPAGAAASSCLE-AGGDGHETWIRVERLEKGLCGAASRPVFFRGVATVV
SEQ ID NO:14     AYPSDFQGDLQKLMSVPGGVDVVFHPHNLYDYGGDGGD-AVAECGDGVVSCVDRRSGFGHETWVRAEKIRKPLCGKSRPVFFRGVATIV
SEQ ID NO:15     TYPSDFAGDLRKLAST-GVVDAVFNPPDLYVRGA--GRRGAGS--GGAISCLEEAAGDGHETWVRVERLEKGLCGASRPVFFRGVATIV
```

FIG. 1A

```
              181                                                                              270
SEQ ID NO:2   AKLFNIVEPDVAVFGKKDYQQWRVICRMVRDLDFAIQIVGSEVVREADGLAMSSRNVNLSEEDRKKALSISRSLVDARTAALSGSNR-SQ
SEQ ID NO:4   AKLFNIVEPDVAVFGKKDYQQWRVICRMVRDLDFAIQIVGSEVVREADGLAMSSRNVNLSEEDRKKALSISRSLVDARTATLSGSNR-SQ
SEQ ID NO:7   TKLFNIVEPDVSVFGKKDYQQWRIIRRLV-NLDFSIQVIGSEVMRDHDGLALSSRNVHLSPEEREKALSISRSLSRAKSAAEKG-QVNCQ
SEQ ID NO:9   TKLFNIVEPDVAVFGKKDYQQWRLIQRMVRDLDFSIKVIGAEITRDNDGLAMSSRNVHLSPEEREKALSINKSLLRAKSAAGDG-QVHCE
SEQ ID NO:11  SKLFHIVEPDVAVFGKKDFQQWRVIEKMVRDLDFPVRIVGSEIVREVDGLAMSSRNVRLTPEEREKALSISRSLSRAKVAAQNGSSS-CC
SEQ ID NO:13  AKLFNVVEPDVAMFGKKDYQQWRLICRMVRDLDFAVELIGAEIVREADGLAMSSRNVHLSPEEREKALSISRSLLNARTAALNNSNSASE
SEQ ID NO:14  TKLFNIVEPDVAVFGKKDYQQWKIIQRMVRDLDFSIKVIGSEVIREKDGLAMSSRNVYLSPEEREKAVSINKSLFRAKSAAEDG-QIHCE
SEQ ID NO:15  SKLFNIIEPDVPVFGKKDYQQWRVILPYWSGLDFGIELMGSRNCARTDGLAMNSRNVHLSREEGKKALSISRSLVDARTGALKG-NTDSK

271
SEQ ID NO:2   EIKDQIVRTITEAGGQVDYVEIVGQESLVPVERMDRPCVICVAAWFGKVRLIDNIEIHVDSSTVLSI             325
SEQ ID NO:4   EIKDQIVRTITEAGCQVDYVEIVEQESLVPVERMDRPCVICVAAWFGKVRLIDNIEIHVDSSTVLSI             323
SEQ ID NO:7   NLKDSVIQAIQEAGGKIDYAEIVDQESLEAVEEIRSPVVSCVAAWFGKVRLIDNIEIN--------V            311
SEQ ID NO:9   KLTNLVIQSVTDAGGRIDYAEIVDQNNLEKVEQIKSPVVFCVAAWFGKVRLIDNMEINLS-----MNV            310
SEQ ID NO:11  ELKDIATQSITEAGGRIDYVEIVDQESLKVVLDITSPVVMCIAAWFGNVRLIDNMEI------TI              296
SEQ ID NO:13  HIKDQIVQTLTEAGGRVDYVEIVEQESLVPVETIDRPVVICVAAWFGKVRLIDNIEIHIQS------             316
SEQ ID NO:14  KLINLVVQSITEAGGRIDYAEIVDQNNLEKVEWIKGPVVFCVSAWFGKARLIDNIEINL--------             308
SEQ ID NO:15  QIKNKIVQTLTETGGQVDYVEIVEGGLVPVEQIDGPVVICVAAWFGKVRLIDNIEIDTRS-------             313
```

FIG. 1B

SEQUENCE LISTING

<160> NUMBER OF SEQ ID NOS: 15

<210> SEQ ID NO 1
<211> LENGTH: 1443
<212> TYPE: DNA
<213> ORGANISM: Zea mays

<400> SEQUENCE: 1

```
ctgctgcatc ccaatcccat ttaaatttta tcgtcaacaa tttcgtcttc tcggtttctg      60
acttattccg gggcattttt tttttcttgt ttcgagcctg tgagtctgat tccatttttga   120
cccatggcgg cggcggcggc ggcggttcat gagccggagg tgatccgcga caaggcggcg    180
atgcgcgcgt ggtcgcgccg ccgccgcgcg gagggaaagg ccgtcgcttt agtcccacg     240
atgggcttcc tccacgaggg acacctctcg ctcatctccg cggccgtggc ggcctccgcc    300
ggccccatcg ccgtcgtcgt ctccatctac gtcaacccca gccagttcgc ccccaccgag    360
gacctcgcca cctaccctc cgacttcgcc ggcgacctcc gcaagctggc cgccaccggg     420
gtcgtcgccg cagtattttg tcccccagac ctctacgtcc gcggcagcgc tgatcgcccc    480
tccgccgccg gcgcgtccgg gggcgcggtg tcttgcctgg aggatgcagg tgggcatgcg    540
cacgagacgt ggattcgggt ggagcggctg gagaaggggc tgtgcgggag cagcaggcct    600
gtcttcttcc gcggcgtggc caccgtggtc gccaagctgt tcaatatcgt ggagccggac    660
gtcgccgtgt tcgggaagaa ggattatcag cagtggcgcg tcatttgtcg gatggttcgt    720
gatctcgatt ttgccataca gatagttggt tcggaagtag tgcgagaagc tgatggtctt    780
gcaatgagct ctcgcaatgt aaatctgtca gaggaggata gaaagaaggc gttatcgatc    840
agtagatcgc tggtggatgc tagaaccgcc gccctcagtg gaagcaaccg tagccaagaa    900
ataaaagatc aaatagtgcg tacaattaca gaagctggcg gtcaggttga ctatgttgag    960
attgtggggc aggaaagctt ggtgcctgtg gagaggatgg accgcccttg tgtaatttgt   1020
gtcgcggcat ggtttggaaa ggtcaggcta attgacaaca tcgagatcca tgtagatagc   1080
tctactgttt tgtctatctg atgaacgaag atgtttagac acacggcaaa atggcatacc   1140
actttctacg tagcagtagc agaccaagaa taaatagcat gatgggctga atctggatag   1200
aagaccatga gctcagtgct agccattctt gaactgctag aatgcagaga ataagtactt   1260
tcacagtttc agtcaagcta aggcagcaca aatgaatctt aggcatctct aaagtactca   1320
acacattggg ggaaaaaga aaggacatta atgactgaat cttcgaagct tgtggttaaa    1380
aaaaaaaaaa aaaaaaaaaa aaaaaaaaaa aaaaaaaaaa aaaaaaaaaa aaaaaaaaaa   1440
aaa                                                                  1443
```

<210> SEQ ID NO 2
<211> LENGTH: 325
<212> TYPE: PRT
<213> ORGANISM: Zea mays

<400> SEQUENCE: 2

```
Met Ala Ala Ala Ala Ala Ala Val His Glu Pro Glu Val Ile Arg Asp
  1               5                  10                  15

Lys Ala Ala Met Arg Ala Trp Ser Arg Arg Arg Ala Glu Gly Lys
             20                  25                  30

Ala Val Ala Leu Val Pro Thr Met Gly Phe Leu His Glu Gly His Leu
         35                  40                  45
```

```
Ser Leu Ile Ser Ala Val Ala Ser Ala Gly Pro Ile Ala Val
    50                  55                  60

Val Val Ser Ile Tyr Val Asn Pro Ser Gln Phe Ala Pro Thr Glu Asp
 65                  70                  75                  80

Leu Ala Thr Tyr Pro Ser Asp Phe Ala Gly Asp Leu Arg Lys Leu Ala
                 85                  90                  95

Ala Thr Gly Val Val Ala Ala Val Phe Cys Pro Pro Asp Leu Tyr Val
            100                 105                 110

Arg Gly Ser Ala Asp Arg Pro Ser Ala Ala Gly Ala Ser Gly Gly Ala
        115                 120                 125

Val Ser Cys Leu Glu Asp Ala Gly Gly His Ala His Glu Thr Trp Ile
    130                 135                 140

Arg Val Glu Arg Leu Glu Lys Gly Leu Cys Gly Ser Ser Arg Pro Val
145                 150                 155                 160

Phe Phe Arg Gly Val Ala Thr Val Val Ala Lys Leu Phe Asn Ile Val
                165                 170                 175

Glu Pro Asp Val Ala Val Phe Gly Lys Lys Asp Tyr Gln Gln Trp Arg
            180                 185                 190

Val Ile Cys Arg Met Val Arg Asp Leu Asp Phe Ala Ile Gln Ile Val
        195                 200                 205

Gly Ser Glu Val Val Arg Glu Ala Asp Gly Leu Ala Met Ser Ser Arg
    210                 215                 220

Asn Val Asn Leu Ser Glu Glu Asp Arg Lys Lys Ala Leu Ser Ile Ser
225                 230                 235                 240

Arg Ser Leu Val Asp Ala Arg Thr Ala Ala Leu Ser Gly Ser Asn Arg
                245                 250                 255

Ser Gln Glu Ile Lys Asp Gln Ile Val Arg Thr Ile Thr Glu Ala Gly
            260                 265                 270

Gly Gln Val Asp Tyr Val Glu Ile Val Gly Gln Glu Ser Leu Val Pro
        275                 280                 285

Val Glu Arg Met Asp Arg Pro Cys Val Ile Cys Val Ala Ala Trp Phe
    290                 295                 300

Gly Lys Val Arg Leu Ile Asp Asn Ile Glu Ile His Val Asp Ser Ser
305                 310                 315                 320

Thr Val Leu Ser Ile
                325

<210> SEQ ID NO 3
<211> LENGTH: 1831
<212> TYPE: DNA
<213> ORGANISM: Zea mays

<400> SEQUENCE: 3
gcacgaggga aaattccttg atttccctct ttatcttctg catcccactc ccatttactg      60
ttctttgttc cgttttctaa tgagccaccg ccgtcttcct tatctgctgc atcccaatcc     120
catttaaatt ttgtcgtcaa caatttcgtc ttctcggttt ctgacttatt ccggggcatt     180 ttttttttctt gtttcgagcc tgtgagcctg attccatttt gacccatggc ggcggcggcg     240
gttcatgagc cggaggtgat ccgcgacaag gcggcgatgc gcgcgtggtc gcgccgccgc     300
cgcgcggagg gaaaggccgt cgctttagtc cccacgatgg gcttcctcca cgagggacac     360
ctctcgctcg tctccgcggc cgtggcggcc tccgccggcc ccgtcgccgt cgtcgtctcc     420
atctacgtca accccagcca gttcgccccc acgaggacc tcgccaccta ccctccgac      480 ttcgccggcg acctcggcaa gctggccgcc accggggtcg tcgccgcagt attttgccccc    540
```

-continued

```
ccggacctct acgtccgcgg cagcgctgac cgcccctccg ccgccagcgc gtccggggc      600 gcggtgtctt gcctggagga tgcaggtggg catgcgcacg agacgtggat cgggtggag      660 cggctggaga aggggctgtg cgggagcagc aggcctgtct tcttccgcgg cgtggccacc      720
gtggtcgcca agctgttcaa tatcgtggag ccggacgtcg ccgtgttcgg gaagaaggat      780
tatcagcagt ggcgcgtcat ttgtcggatg gttcgtgatc ttgattttgc catacagata      840
gttggttcgg aggtagtgcg agaagctgat ggtcttgcaa tgagctctcg caatgtaaat      900
ctgtcagagg aggatagaaa gaaggcgtta tcgatcagta gatcactggt ggatgctaga      960
accgccaccc tcagtggaag caaccgtagc caagagataa aagatcaaat agtgcggaca     1020
attacagaag ctggcggtca ggttgactat gttgagattg tggagcagga agcttggtg     1080 cctgtggaga ggatggaccg cccttgtgta atttgtgtcg cggcatggtt tggaaaggtc     1140
aggctaattg acaacatcga gatccatgta gatagctcta ctgttttgtc tatctgatga     1200
acgaagatgt ttagacacgg caaaatggca taccactttc tacgtagcag tagcagacca     1260 agaataaaata gcatgatggg ctgaatctgg atagaagacc atgagctcag tgctagccat     1320
tcttgaactg ctagaatgca gagaataagt actttcacag tttcagtcaa gctaaggcag     1380
cacaaatgaa tcttaggcat ctctaaagta ctcaacacat tggggaaaa agaaaggac     1440 attaatgact gaatcttcga agcttgtgat acattccttt aaaaaaaaac agatttaca     1500 ttagcttctc tcgttagtca ccagatgcac tctatagtta ccggaggctc aagggcgctt     1560
aaaatctcaa gcatgagcaa tcaatctggc cggacatctt ggttctcaac tgcccattga     1620
tacttgattc aagcactctg ccaataacaa aactactcga actccagcag ctccctgtct     1680
cgctcactat cttaaactcc atgcggtaaa cagtataaaa acagtgtttt gtacatccat     1740
atacatgatc cgccgaagac ggtctaaggt tgcataaatg tatttctctt tttgttgttt     1800
taaaaaaaaa aaaaaaaaaa aaaaaaaaaa a                                    1831
```

<210> SEQ ID NO 4
<211> LENGTH: 323
<212> TYPE: PRT
<213> ORGANISM: Zea mays

<400> SEQUENCE: 4

```
Met Ala Ala Ala Val His Glu Pro Glu Val Ile Arg Asp Lys Ala
  1               5                  10                  15

Ala Met Arg Ala Trp Ser Arg Arg Arg Ala Glu Gly Lys Ala Val
                 20                  25                  30

Ala Leu Val Pro Thr Met Gly Phe Leu His Glu Gly His Leu Ser Leu
             35                  40                  45

Val Ser Ala Ala Val Ala Ala Ser Ala Gly Pro Val Ala Val Val
         50                  55                  60

Ser Ile Tyr Val Asn Pro Ser Gln Phe Ala Pro Thr Glu Asp Leu Ala
 65                  70                  75                  80

Thr Tyr Pro Ser Asp Phe Ala Gly Asp Leu Gly Lys Leu Ala Ala Thr
                 85                  90                  95

Gly Val Val Ala Ala Val Phe Cys Pro Pro Asp Leu Tyr Val Arg Gly
            100                 105                 110

Ser Ala Asp Arg Pro Ser Ala Ala Ser Ala Ser Gly Gly Ala Val Ser
        115                 120                 125

Cys Leu Glu Asp Ala Gly Gly His Ala His Glu Thr Trp Ile Arg Val
    130                 135                 140
```

-continued

```
Glu Arg Leu Glu Lys Gly Leu Cys Gly Ser Ser Arg Pro Val Phe Phe
145                 150                 155                 160

Arg Gly Val Ala Thr Val Ala Lys Leu Phe Asn Ile Val Glu Pro
            165                 170                 175

Asp Val Ala Val Phe Gly Lys Lys Asp Tyr Gln Gln Trp Arg Val Ile
            180                 185                 190

Cys Arg Met Val Arg Asp Leu Asp Phe Ala Ile Gln Ile Val Gly Ser
            195                 200                 205

Glu Val Val Arg Glu Ala Asp Gly Leu Ala Met Ser Ser Arg Asn Val
            210                 215                 220

Asn Leu Ser Glu Glu Asp Arg Lys Lys Ala Leu Ser Ile Ser Arg Ser
225                 230                 235                 240

Leu Val Asp Ala Arg Thr Ala Thr Leu Ser Gly Ser Asn Arg Ser Gln
                245                 250                 255

Glu Ile Lys Asp Gln Ile Val Arg Thr Ile Thr Glu Ala Gly Gly Gln
            260                 265                 270

Val Asp Tyr Val Glu Ile Val Glu Gln Glu Ser Leu Val Pro Val Glu
275                 280                 285

Arg Met Asp Arg Pro Cys Val Ile Cys Val Ala Ala Trp Phe Gly Lys
            290                 295                 300

Val Arg Leu Ile Asp Asn Ile Glu Ile His Val Asp Ser Ser Thr Val
305                 310                 315                 320

Leu Ser Ile
        323

<210> SEQ ID NO 5
<211> LENGTH: 1644
<212> TYPE: DNA
<213> ORGANISM: Eucalyptus grandis

<400> SEQUENCE: 5
gaaaccactg aagacccgct tgcattctcc ttcttgcctt acccaaattc ctgctgctct      60
ccctctccca tccgatccca cgaaattccc ttctttccaa tcccttccgg tgtcctcctc    120
caatggcggc gccccccaag gagccgctgg tcatcaccga caaggccgag atgcgggagt    180
ggtcgaggtc cgcgcggcgc cagggcagga ccatcgccct cgtgcccacc atgggttttcc   240
tccacgaggg ccacctgtcc ctcgtccggg aggcccgccg ccgcgccgac gccgtcgtgg    300
tctccgtcta cgtgaacccc ggccagttcg cccctccga ggacctctcg acgtacccat     360
ctgatttcga gggcgacctg gcaagctca gggccgtccc cggcggcgtg gacgtcgtct     420
ttcgtcccca gaatctttac gactacggtc aacgcgaggt cggtggctct ggcgttgaga    480
gcgataatgg gtccgtgtct tgtttggagg agaagggcat ggggcacgag cgtgggtga    540
gggtggagag gttggagaag gcatgtgcg gaagagcag gcccgtgttc tttcgagggg    600
tggccactgt ggtcaccaag ctgttcaaca ttgtggagcc ggatgtgagt gttttcggga    660
agaaggatta ccagcagtgg cggatcattc ggcggttggt gagtctcttc tattcgaatt    720
cgagcatcgg taattcgggt gtggcgggac aaagggctga agctgagaaa agtacattac    780
tcttccaatt tgtatgatag ccttgcttgt cgaatggagt cattgtcagt gcatatgcca    840
gtttcggagt tgttggcggt ttttggcggt gactatgact caattggcag agtggtggta    900
ttagatttaa tttgaaaatc tgatggtgtt ttagtcatag gtgaaagatt ctgttctatg    960
ctcctgggaa ggctggttgc taatgatttg gattgctgtt gttctttga tgttctgctg  1020
```

```
ccacatatgg agatgcgttt acttcatatt tctgaacaga aagtttgagg ctgcttggct    1080
atgaacgtta tttgtggatt gggattttta ctctgttaca actatgttga gtaattcaac    1140
atgaggagct tcaacggttc aagatcttga cttttccata caagtgatag gttctgaggt    1200
catgcgagat catgatggcc ttgcgctaag ctcacgcaat gtgcatctct cacctgaaga    1260
aagggaaaag gcattgtcca taagcaggtc attgtcaaga gctaaatctg ctgcggaaaa    1320
gggtcaagtt aactgccaaa atctaaagga ctccgtcatc caagcaatac aggaagctgg    1380
tgggaagatt gattatgctg agattgtaga tcaagagagt ttagaggcag ttgaagaaat    1440
caggagcccc gtcgtctcct gtgtcgccgc ctggtttggg aaggtcaggc tgattgataa    1500
catagaaatc aatgtatgaa ggaacacctt tgtgctcgtc atctcatcat gaggaagggt    1560 tctcttttc tttctgcttc tgtggcagcc gaaatgactg tctctgtcg gtggcattta     1620 cacgataaaa aaaaaaaaa aaaa                                           1644

<210> SEQ ID NO 6
<211> LENGTH: 1183
<212> TYPE: DNA
<213> ORGANISM: Eucalyptus grandis

<400> SEQUENCE: 6
gaaaccactg aagacccgct tgcattctcc ttcttgcctt acccaaattc ctgctgctct     60
ccctctccca tccgatccca cgaaattccc ttctttccaa tcccttccgg tgtcctcctc    120
caatggcggc gccccccaag gagccgctgg tcatcaccga caaggccgag atgcgggagt    180
ggtcgaggtc cgcgcggcgc cagggcagga ccatcgccct cgtgcccacc atgggtttcc    240
tccacgaggg ccacctgtcc ctcgtccggg aggcccgccg ccgcgccgac gccgtcgtgg    300
tctccgtcta cgtgaacccc ggccagttcg ccccctccga ggacctctcg acgtacccat    360
ctgatttcga gggcgacctg gcaagctca gggccgtccc cggcggcgtg gacgtcgtct    420
tcgtccccca gaatctttac gactacggtc aacgcgaggt cggtggctct ggcgttgaga    480
gcgataatgg gtccgtgtct tgtttggagg agaagggcat ggggcacgag gcgtgggtga    540
gggtggagag gttggagaag gcatgtgcg ggaagagcag gcccgtgttc tttcgagggg    600
tggccactgt ggtcaccaag ctgttcaaca ttgtggagcc ggatgtgagt gttttcggga    660
agaaggatta ccagcagtgg cggatcattc ggcggttggt gaatcttgac ttttccatac    720
aagtgatagg ttctgaggtc atgcgagatc atgatggcct tgcgctaagc tcacgcaatg    780
tgcatctctc acctgaagaa agggaaaagg cattgtccat aagcaggtca ttgtcaagag    840
ctaaatctgc tgcggaaaag ggtcaagtta actgccaaaa tctaaaggac tccgtcatcc    900
aagcaataca ggaagctggt gggaagattg attatgctga gattgtagat caagagagtt    960
tagaggcagt tgaagaaatc aggagccccg tcgtctcctg tgtcgccgcc tggtttggga   1020
aggtcaggct gattgataac atagaaatca atgtatgaag gaacaccttt gtgctcgtca   1080
tctcatcatg aggaagggtt ctcttttct ttctgcttct gtggcagccg aaatgactgg    1140
tctctgtcgg tggcatttac acgataaaaa aaaaaaaaaa aaa                     1183

<210> SEQ ID NO 7
<211> LENGTH: 311
<212> TYPE: PRT
<213> ORGANISM: Eucalyptus grandis

<400> SEQUENCE: 7

Met Ala Ala Pro Pro Lys Glu Pro Leu Val Ile Thr Asp Lys Ala Glu
```

```
  1               5               10              15
Met Arg Glu Trp Ser Arg Ser Ala Arg Arg Gln Gly Arg Thr Ile Ala
                20              25              30

Leu Val Pro Thr Met Gly Phe Leu His Glu Gly His Leu Ser Leu Val
                35              40              45

Arg Glu Ala Arg Arg Ala Asp Ala Val Val Ser Val Tyr Val
        50              55              60

Asn Pro Gly Gln Phe Ala Pro Ser Glu Asp Leu Ser Thr Tyr Pro Ser
 65             70              75              80

Asp Phe Glu Gly Asp Leu Gly Lys Leu Arg Ala Val Pro Gly Gly Val
                85              90              95

Asp Val Val Phe Arg Pro Gln Asn Leu Tyr Asp Tyr Gly Gln Arg Glu
                100             105             110

Val Gly Gly Ser Gly Val Glu Ser Asp Asn Gly Ser Val Ser Cys Leu
                115             120             125

Glu Glu Lys Gly Met Gly His Glu Ala Trp Val Arg Val Glu Arg Leu
 130            135             140

Glu Lys Gly Met Cys Gly Lys Ser Arg Pro Val Phe Phe Arg Gly Val
145             150             155             160

Ala Thr Val Val Thr Lys Leu Phe Asn Ile Val Glu Pro Asp Val Ser
                165             170             175

Val Phe Gly Lys Lys Asp Tyr Gln Gln Trp Arg Ile Ile Arg Arg Leu
                180             185             190

Val Asn Leu Asp Phe Ser Ile Gln Val Ile Gly Ser Glu Val Met Arg
            195             200             205

Asp His Asp Gly Leu Ala Leu Ser Ser Arg Asn Val His Leu Ser Pro
 210            215             220

Glu Glu Arg Glu Lys Ala Leu Ser Ile Ser Arg Ser Leu Ser Arg Ala
225             230             235             240

Lys Ser Ala Ala Glu Lys Gly Gln Val Asn Cys Gln Asn Leu Lys Asp
                245             250             255

Ser Val Ile Gln Ala Ile Gln Glu Ala Gly Gly Lys Ile Asp Tyr Ala
                260             265             270

Glu Ile Val Asp Gln Glu Ser Leu Glu Ala Val Glu Glu Ile Arg Ser
            275             280             285

Pro Val Val Ser Cys Val Ala Ala Trp Phe Gly Lys Val Arg Leu Ile
 290            295             300

Asp Asn Ile Glu Ile Asn Val
305             310
```

<210> SEQ ID NO 8
<211> LENGTH: 1316
<212> TYPE: DNA
<213> ORGANISM: Glycine max

<400> SEQUENCE: 8

```
tcggcacgag gctttctcag caggaggcct cgtgccgtac acaccaaaac gtacttcaac     60
ccaaagagtc ataataactt tgcctaacac ctacctcttc aaccaccgcg ttcgcgccat    120
cacgttcgtc ctttcactta ttacactcct cacgaaactc ccactgtttc aatattatt    180
cacaatggct ccagccccaa gggtgatctc cgacaaggcc tcgatgcgga gctggtcgcg    240
ctcgatgcgg gcccagggca agctcattgg gctggtcccc accatgggct tcctccacgc    300
gggccacctc tcgctcgtgg cccaggcccg ccaactctcc gacgtcgtcg ccgtctccat    360
```

-continued

| | |
|---|---|
| ctacgtcaac ccgggccaat tcgcccccac ggaggacctc tccacctacc cctccgactt | 420 |
| cgacggcgac gtaaagaaac tcgcgtccgt tcccggcggc gtcgacgtcg ttttccatcc | 480 |
| ccgtaacttg tacgattacg ggaagaacgg tggtggtgac gtggcagagg ctggtggaat | 540 |
| ggtgtcgtgc gttgagagtg ggtccgggca cgaaagttgg gtgaggggttg agaagctgga | 600 |
| attggggctg tgtgggaaga gcaggcccgt tttcttcaga ggggtggcga ctgtggtgac | 660 |
| gaagttgttt aatattgtgg agccagatgt ggctgtgttc ggtaagaagg attatcagca | 720 |
| gtggcggctt attcagagga tggttcgaga tcttgatttt tccataaaag tgataggtgc | 780 |
| tgaaataaca cgtgataatg atggcctggc aatgagttca cgtaatgtgc acctttcacc | 840 |
| tgaagagagg gaaaaggcac tatcaataaa taaatcattg ttaagagcta atcagcagc | 900 |
| aggagatggt caggtgcatt gtgagaagtt gacaaatttg gtcatccaaa gtgttactga | 960 |
| tgctggtgga aggatcgatt atgctgagat tgttgatcaa ataatttgg agaaagtgga | 1020 |
| acagatcaag agtcctgtcg tcttctgtgt tgctgcatgg tttggcaaag tcaggcttat | 1080 |
| agacaacatg gaaatcaact tgtcaatgaa tgtttgatct aaccttctgt catctcaaac | 1140 |
| atgggccaca tgcttaatta atagttcggg ccacgtgctt aacaattcta acagttcatg | 1200 |
| gttatagtca tgacaatttt tttttctgcc agccatacat gattacttgt agatgcattt | 1260 |
| taccgcatca taaaattcta tgagagctgc taccagtggc attgctattt gctagg | 1316 |

<210> SEQ ID NO 9
<211> LENGTH: 310
<212> TYPE: PRT
<213> ORGANISM: Glycine max

<400> SEQUENCE: 9

Met Ala Pro Ala Pro Arg Val Ile Ser Asp Lys Ala Ser Met Arg Ser
1               5                   10                  15

Trp Ser Arg Ser Met Arg Ala Gln Gly Lys Leu Ile Gly Leu Val Pro
            20                  25                  30

Thr Met Gly Phe Leu His Ala Gly His Leu Ser Leu Val Ala Gln Ala
        35                  40                  45

Arg Gln Leu Ser Asp Val Val Ala Val Ser Ile Tyr Val Asn Pro Gly
    50                  55                  60

Gln Phe Ala Pro Thr Glu Asp Leu Ser Thr Tyr Pro Ser Asp Phe Asp
65                  70                  75                  80

Gly Asp Val Lys Lys Leu Ala Ser Val Pro Gly Gly Val Asp Val Val
                85                  90                  95

Phe His Pro Arg Asn Leu Tyr Asp Tyr Gly Lys Asn Gly Gly Gly Asp
            100                 105                 110

Val Ala Glu Ala Gly Gly Met Val Ser Cys Val Glu Ser Gly Ser Gly
        115                 120                 125

His Glu Ser Trp Val Arg Val Glu Lys Leu Glu Leu Gly Leu Cys Gly
    130                 135                 140

Lys Ser Arg Pro Val Phe Phe Arg Gly Val Ala Thr Val Val Thr Lys
145                 150                 155                 160

Leu Phe Asn Ile Val Glu Pro Asp Val Ala Val Phe Gly Lys Lys Asp
                165                 170                 175

Tyr Gln Gln Trp Arg Leu Ile Gln Arg Met Val Arg Asp Leu Asp Phe
            180                 185                 190

Ser Ile Lys Val Ile Gly Ala Glu Ile Thr Arg Asp Asn Asp Gly Leu
        195                 200                 205

-continued

```
Ala Met Ser Ser Arg Asn Val His Leu Ser Pro Glu Glu Arg Glu Lys
    210                 215                 220

Ala Leu Ser Ile Asn Lys Ser Leu Leu Arg Ala Lys Ser Ala Ala Gly
225                 230                 235                 240

Asp Gly Gln Val His Cys Glu Lys Leu Thr Asn Leu Val Ile Gln Ser
                245                 250                 255

Val Thr Asp Ala Gly Gly Arg Ile Asp Tyr Ala Glu Ile Val Asp Gln
            260                 265                 270

Asn Asn Leu Glu Lys Val Glu Gln Ile Lys Ser Pro Val Phe Cys
        275                 280                 285

Val Ala Ala Trp Phe Gly Lys Val Arg Leu Ile Asp Asn Met Glu Ile
    290                 295                 300

Asn Leu Ser Met Asn Val
305                 310
```

<210> SEQ ID NO 10
<211> LENGTH: 1148
<212> TYPE: DNA
<213> ORGANISM: Tulipa fosteriana

<400> SEQUENCE: 10

```
gcacgagcca ttctccgtcc tctccttcac caatggccgc cgcccccgcc gcctcgtccg     60
ccgccgccgc ctccgtctcg gaaccagtca taattacctc gaaacccgag atgctagcct   120
ggtcccggca ccaccggcgc ctctcccaca ccatcgccct cgtccccacc atgggctccc   180
tccacgccgg ccatctctcc ctcatctccc atgccgcctc cctcgccgac ctcaccgtcg   240
tctccatcta cctcaacccc acccagttcg cccctccga ggacctcgcc acctaccccg    300
ccgacctcgc cgccgacctc cgcaacctcc gcgcctgccc ctccgtcgcc gccgtcttct   360
gccccactaa tccctacgcg gacgggcacg agacgtgggt gagggtggag gagctggagc   420
gggggctgtg cgggctgagc cggccggtgt tttttcgggg tgtcgcgacg gtggtgtcga   480
agctgtttca tttggtggag cccgatgtcg cggtgttcgg aagaaggat tttcagcagt    540
ggcgggtgat cgagaaatg gtacgcgatc ttgattttcc tgtaaggatt gttggatctg    600
aaatagtacg ggaggttgat ggactcgcca tgagctcacg taatgttcgc ctaacacctg   660
aagagcgaga aaaagcactg tccattagta gatctctctc tcgagcaaaa gttgctgcac   720
aaaatgggag cagcagctgc caagaactta agatatagc cactcaaagc ataacagagg    780
ctggtggtag aattgattat gtcgagattg tagatcagga gagtttgaaa gtggtgttgg   840
atattacaag ccctgtcgtg atgtgcattg ctgcttggtt tggaaatgtt aggttgattg   900
acaacatgga atcactata tgaagctgat gcggtttgag gatgatacaa tgttatggcc    960
acatagatcc tttctatcaa tctcttgagt tctgcaatcg gcgaatcctg atttccaact  1020
gttgttgggc catcaagatg agtggtattt caacattgag tggtatgtga gcattttatg  1080
tatgtacatg atgagttcct caaaaaaaaa aaaaaaaaa aaaaaaaaa aaaaaaaaa      1140
aaaaaaaa                                                            1148
```

<210> SEQ ID NO 11
<211> LENGTH: 296
<212> TYPE: PRT
<213> ORGANISM: Tulipa fosteriana

<400> SEQUENCE: 11

```
Met Ala Ala Ala Pro Ala Ala Ser Ser Ala Ala Ala Ser Val Ser
  1                 5                 10                 15
```

```
Glu Pro Val Ile Ile Thr Ser Lys Pro Glu Met Leu Ala Trp Ser Arg
         20                  25                  30

His His Arg Arg Leu Ser His Thr Ile Ala Leu Val Pro Thr Met Gly
     35                  40                  45

Ser Leu His Ala Gly His Leu Ser Leu Ile Ser His Ala Ala Ser Leu
 50                  55                  60

Ala Asp Leu Thr Val Val Ser Ile Tyr Leu Asn Pro Thr Gln Phe Ala
 65                  70                  75                  80

Pro Ser Glu Asp Leu Ala Thr Tyr Pro Ala Asp Leu Ala Ala Asp Leu
                 85                  90                  95

Arg Asn Leu Arg Ala Cys Pro Ser Val Ala Ala Val Phe Cys Pro Thr
             100                 105                 110

Asn Pro Tyr Ala Asp Gly His Glu Thr Trp Val Arg Val Glu Glu Leu
         115                 120                 125

Glu Arg Gly Leu Cys Gly Leu Ser Arg Pro Val Phe Phe Arg Gly Val
     130                 135                 140

Ala Thr Val Val Ser Lys Leu Phe His Leu Val Glu Pro Asp Val Ala
145                 150                 155                 160

Val Phe Gly Lys Lys Asp Phe Gln Gln Trp Arg Val Ile Glu Lys Met
                 165                 170                 175

Val Arg Asp Leu Asp Phe Pro Val Arg Ile Val Gly Ser Glu Ile Val
             180                 185                 190

Arg Glu Val Asp Gly Leu Ala Met Ser Ser Arg Asn Val Arg Leu Thr
         195                 200                 205

Pro Glu Glu Arg Glu Lys Ala Leu Ser Ile Ser Arg Ser Leu Ser Arg
     210                 215                 220

Ala Lys Val Ala Ala Gln Asn Gly Ser Ser Ser Cys Gln Glu Leu Lys
225                 230                 235                 240

Asp Ile Ala Thr Gln Ser Ile Thr Glu Ala Gly Gly Arg Ile Asp Tyr
                 245                 250                 255

Val Glu Ile Val Asp Gln Glu Ser Leu Lys Val Val Leu Asp Ile Thr
             260                 265                 270

Ser Pro Val Val Met Cys Ile Ala Ala Trp Phe Gly Asn Val Arg Leu
         275                 280                 285

Ile Asp Asn Met Glu Ile Thr Ile
         290                 295

<210> SEQ ID NO 12
<211> LENGTH: 1235
<212> TYPE: DNA
<213> ORGANISM: Triticum aestivum

<400> SEQUENCE: 12
gcacgagctc gtgccgaatt cggcacgagc tcatctgacc aatttgactg ctctgctccc      60
gatcccatgg cggcggcggg cgagccggag gtgatccggg acaaggcggc gatgcgggcg     120
tggtcgcggc gccagcgggc ggagggaaag acggtggtgc tcgtgcccac catgggcttc     180
ctccacgagg gccacctctc gctcgtctcc gccgcgcgcg ccgtgcccgg ccccgtcgcc     240
gtcgtcgtct ccatctacgt caaccccagc cagttcgccc ccaccgagga cctcgccacc     300
taccccctcc gacctcgccgg ggacctccgc aagctcgcct ccaccggcgc cgtccacgcc     360
gtcttcaacc cccagacct ctaccaccgc ggcgccgctg tctctggccg ccgcgccgag     420
gctcccgccg gcgccgctgc ctcttcctgc ctggaggcgg gcggggacgg gcacgagact     480
```

-continued

```
tggatccggg tggagcggct ggagaagggc ctctgtgggg ccagccggcc agtgttcttc    540
cgtggggtgg ccaccgtcgt cgccaagctg ttcaacgtcg ttgagcccga cgtcgccatg    600
ttcgggaaga aggattacca gcagtggcgc ctcatctgcc gaatggttcg tgaccttgat    660
tttgccgtag agataatagg agcagaaata gtgcgagaag cagatggtct tgccatgagc    720
tctcgcaacg tccacctctc gcctgaggaa agggagaagg cattatccat tagtagatca    780
ctgttaaatg ctagaactgc tgcgttgaat aatagcaaca gtgctagcga acatataaag    840
gatcagatag tgcagacgct gactgaagct ggcggtcggg ttgattatgt tgagattgtg    900
gagcaggaaa gtttggtacc tgtggagacg atcgaccgcc ctgttgtcat ttgtgtcgcc    960
gcatggtttg gaaaggttag attgatcgat aatatcgaaa ttcatataca atcctgagga   1020
ttttgctgtc gccttgtata cgtatctcat gaagtatcac caatctgtat ttctgtcaaa   1080
aataagaatg atgttgtaca atgtaagttt gtaacaacca cgtacagaga acttgcaaaa   1140
tcttcgataa atgtcttcat ttattgtttc aatgatagat atgttgctat gccaaaaaaa   1200
aaaaaaaaaa aaaaaaaaaa aaaaaaaaaa aaaaa                              1235
```

<210> SEQ ID NO 13
<211> LENGTH: 316
<212> TYPE: PRT
<213> ORGANISM: Triticum aestivum

<400> SEQUENCE: 13

```
Met Ala Ala Ala Gly Glu Pro Glu Val Ile Arg Asp Lys Ala Ala Met
 1               5                  10                  15

Arg Ala Trp Ser Arg Arg Gln Arg Ala Glu Gly Lys Thr Val Val Leu
            20                  25                  30

Val Pro Thr Met Gly Phe Leu His Glu Gly His Leu Ser Leu Val Ser
        35                  40                  45

Ala Ala Ala Ala Val Pro Gly Pro Val Ala Val Val Ser Ile Tyr
    50                  55                  60

Val Asn Pro Ser Gln Phe Ala Pro Thr Glu Asp Leu Ala Thr Tyr Pro
65                  70                  75                  80

Ser Asp Leu Ala Gly Asp Leu Arg Lys Leu Ala Ser Thr Gly Ala Val
                85                  90                  95

His Ala Val Phe Asn Pro Pro Asp Leu Tyr His Arg Gly Ala Ala Val
            100                 105                 110

Ser Gly Arg Arg Ala Glu Ala Pro Ala Gly Ala Ala Ala Ser Ser Cys
        115                 120                 125

Leu Glu Ala Gly Gly Asp Gly His Glu Thr Trp Ile Arg Val Glu Arg
    130                 135                 140

Leu Glu Lys Gly Leu Cys Gly Ala Ser Arg Pro Val Phe Phe Arg Gly
145                 150                 155                 160

Val Ala Thr Val Val Ala Lys Leu Phe Asn Val Val Glu Pro Asp Val
                165                 170                 175

Ala Met Phe Gly Lys Lys Asp Tyr Gln Gln Trp Arg Leu Ile Cys Arg
            180                 185                 190

Met Val Arg Asp Leu Asp Phe Ala Val Glu Ile Ile Gly Ala Glu Ile
        195                 200                 205

Val Arg Glu Ala Asp Gly Leu Ala Met Ser Ser Arg Asn Val His Leu
    210                 215                 220

Ser Pro Glu Glu Arg Glu Lys Ala Leu Ser Ile Ser Arg Ser Leu Leu
225                 230                 235                 240
```

```
Asn Ala Arg Thr Ala Ala Leu Asn Asn Ser Asn Ser Ala Ser Glu His
            245                 250                 255

Ile Lys Asp Gln Ile Val Gln Thr Leu Thr Glu Ala Gly Gly Arg Val
            260                 265                 270

Asp Tyr Val Glu Ile Val Glu Gln Glu Ser Leu Val Pro Val Glu Thr
            275                 280                 285

Ile Asp Arg Pro Val Val Ile Cys Val Ala Ala Trp Phe Gly Lys Val
            290                 295                 300

Arg Leu Ile Asp Asn Ile Glu Ile His Ile Gln Ser
305                 310                 315

<210> SEQ ID NO 14
<211> LENGTH: 313
<212> TYPE: PRT
<213> ORGANISM: Oryza sativa

<400> SEQUENCE: 14

Met Ala Ala Pro Arg Glu Pro Glu Val Ile Arg Asp Lys Ala Ala Met
1               5                   10                  15

Arg Ala Trp Ser Arg Arg Arg Ala Glu Gly Lys Thr Val Ala Val
            20                  25                  30

Val Pro Thr Met Gly Tyr Leu His Gln Gly His Leu Ser Leu Ile Ser
            35                  40                  45

Ala Ala Ala Ala Ala Ser Ala Asp Pro Val Ala Ile Val Val Thr
            50                  55                  60

Ile Tyr Val Asn Pro Ser Gln Phe Ala Pro Ser Glu Asp Leu Ala Thr
65                  70                  75                  80

Tyr Pro Ser Asp Phe Ala Gly Asp Leu Arg Lys Leu Ala Ser Thr Gly
                85                  90                  95

Val Val Asp Ala Val Phe Asn Pro Pro Asp Leu Tyr Val Arg Gly Ala
            100                 105                 110

Gly Arg Gly Ala Gly Ser Gly Ala Ile Ser Cys Leu Glu Glu
            115                 120                 125

Ala Ala Gly Asp Gly His Glu Thr Trp Val Arg Val Glu Arg Leu Glu
130                 135                 140

Lys Gly Leu Cys Gly Ala Ser Arg Pro Val Phe Phe Arg Gly Val Ala
145                 150                 155                 160

Thr Ile Val Ser Lys Leu Phe Asn Ile Ile Glu Pro Asp Val Pro Val
            165                 170                 175

Phe Gly Lys Lys Asp Tyr Gln Gln Trp Arg Val Ile Leu Pro Tyr Trp
            180                 185                 190

Ser Gly Leu Asp Phe Gly Ile Glu Ile Met Gly Ser Arg Asn Cys Ala
            195                 200                 205

Arg Thr Asp Gly Leu Ala Met Asn Ser Arg Asn Val His Leu Ser Arg
            210                 215                 220

Glu Glu Gly Lys Lys Ala Leu Ser Ile Ser Arg Ser Leu Val Asp Ala
225                 230                 235                 240

Arg Thr Gly Ala Leu Lys Gly Asn Thr Asp Ser Lys Gln Ile Lys Asn
            245                 250                 255

Lys Ile Val Gln Thr Leu Thr Glu Thr Gly Gly Gln Val Asp Tyr Val
            260                 265                 270

Glu Ile Val Glu Gln Glu Ser Leu Val Pro Val Glu Gln Ile Asp Gly
            275                 280                 285

Pro Val Val Ile Cys Val Ala Ala Trp Phe Gly Lys Val Arg Leu Ile
            290                 295                 300
```

```
Asp Asn Ile Glu Ile Asp Thr Arg Ser
305                 310

<210> SEQ ID NO 15
<211> LENGTH: 308
<212> TYPE: PRT
<213> ORGANISM: Lotus japonicus

<400> SEQUENCE: 15

Met Ala Pro Met Val Ile Ser Asp Lys Asp Glu Met Arg Lys Trp Ser
1               5                   10                  15

Arg Ser Met Arg Ser Gln Gly Lys Leu Ile Ala Leu Val Pro Thr Met
            20                  25                  30

Gly Phe Leu His Glu Gly His Leu Ser Leu Val Arg Asp Ala His Asn
            35                  40                  45

His Ala Asp Leu Val Ala Val Ser Ile Tyr Val Asn Pro Gly Gln Phe
        50                  55                  60

Ser Pro Thr Glu Asp Leu Ser Ala Tyr Pro Ser Asp Phe Gln Gly Asp
65                  70                  75                  80

Leu Gln Lys Leu Met Ser Val Pro Gly Gly Val Asp Val Val Phe His
                85                  90                  95

Pro His Asn Leu Tyr Asp Tyr Gly Gly Asp Gly Gly Asp Ala Val Ala
            100                 105                 110

Glu Cys Gly Gly Asp Gly Val Val Ser Cys Val Asp Arg Arg Ser Gly
        115                 120                 125

Phe Gly His Glu Thr Trp Val Arg Ala Glu Lys Leu Glu Lys Pro Leu
130                 135                 140

Cys Gly Lys Ser Arg Pro Val Phe Phe Arg Gly Val Ala Thr Ile Val
145                 150                 155                 160

Thr Lys Leu Phe Asn Ile Val Glu Pro Asp Val Ala Val Phe Gly Lys
                165                 170                 175

Lys Asp Tyr Gln Gln Trp Lys Ile Ile Gln Arg Met Val Arg Asp Leu
            180                 185                 190

Asp Phe Ser Ile Lys Val Ile Gly Ser Glu Val Ile Arg Glu Lys Asp
        195                 200                 205

Gly Leu Ala Met Ser Ser Arg Asn Val Tyr Leu Ser Pro Glu Glu Arg
    210                 215                 220

Glu Lys Ala Val Ser Ile Asn Lys Ser Leu Phe Arg Ala Lys Ser Ala
225                 230                 235                 240

Ala Glu Asp Gly Gln Ile His Cys Glu Lys Leu Ile Asn Leu Val Val
                245                 250                 255

Gln Ser Ile Thr Glu Ala Gly Gly Arg Ile Asp Tyr Ala Glu Ile Val
            260                 265                 270

Asp Gln Asn Asn Leu Glu Lys Val Glu Trp Ile Lys Gly Pro Val Val
        275                 280                 285

Phe Cys Val Ser Ala Trp Phe Gly Lys Ala Arg Leu Ile Asp Asn Ile
    290                 295                 300

Glu Ile Asn Leu
305
```

PLANT GENES ENCODING PANTOTHENATE SYNTHETASE

This application claims the benefit of U.S. Provisional Application No. 60/247,938, filed Nov. 13, 2000, the entire contents of which are herein incorporated by reference.

FIELD OF THE INVENTION

This invention is in the field of plant molecular biology. More specifically, this invention pertains to nucleic acid fragments encoding pantothenate synthetase in plants and seeds.

BACKGROUND OF THE INVENTION

Essential compounds like coenzyme A, acyl carrier protein, and metabolic cofactors share a common precursor molecule, namely pantothenate (also known as vitamin $B_5$). The synthesis of pantothenate from pantoate and alanine is performed by the enzyme pantothenate synthetase. This enzyme is found in bacteria, plants, and fungi but is missing from humans who must get pantothenate from their diet (as noted by its "vitamin" designation). Recent work has identified two plant genes encoding functional pantothenate synthetase from rice and lotus (Genschel, U. et al. (1999) *Biochem J* 341:669–678, and PCT application WO 99/42565 published Aug. 26, 1999).

There is a desire to have pantothenate synthase genes from other plants, particularly from economically important crop plants. These genes, in combination with plant transformation techniques, will enable the production of new corn, soy, wheat, tulip, and eucalyptus plants that have altered pantothenate synthetase activities.

SUMMARY OF THE INVENTION

The present invention is related to six previously unidentified plant pantothenate synthetase cDNAs from corn, eucalyptus, soybean, tulip, and wheat. There are two closely related cDNAs isolated from corn. In a first embodiment, the present invention concerns an isolated polynucleotide comprising: (a) a nucleotide sequence encoding a polypeptide comprising at least 296 amino acids, wherein the amino acid sequence of the polypeptide and the amino acid sequence of SEQ ID NO:2, 4, 7, 9, 11, or 13 have at least 80%, 85%, 90%, or 95% identity based on the Clustal alignment method, or (b) the complement of the nucleotide sequence, wherein the complement and the nucleotide sequence contain the same number of nucleotides and are 100% complementary. The polypeptide preferably comprises the amino acid sequence of SEQ ID NO:2, 4, 7, 9, 11, or 13. The nucleotide sequence preferably comprises the nucleotide sequence of SEQ ID NO:1, 3, 5, 6, 8, 10, or 12. The polypeptide preferably is a pantothenate synthetase.

In a second embodiment, the present invention relates to a chimeric gene comprising any of the isolated polynucleotides of the present invention operably linked to a regulatory sequence, and a cell, a plant, and a seed comprising the chimeric gene.

In a third embodiment, the present invention relates to a vector comprising any of the isolated polynucleotides of the present invention.

In a fourth embodiment, the present invention relates to an isolated polynucleotide comprising a nucleotide sequence comprised by any of the polynucleotides of the first embodiment, wherein the nucleotide sequence contains at least 30, 40, or 60 nucleotides, and a cell, a plant, and a seed comprising the isolated polynucleotide.

In a fifth embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a sixth embodiment, the present invention relates to a method for producing a transgenic plant comprising transforming a plant cell with any of the isolated polynucleotides of the present invention and regenerating a plant from the transformed plant cell, the transgenic plant produced by this method, and the seed obtained from this transgenic plant.

In a seventh embodiment, the present invention concerns an isolated polypeptide comprising an amino acid sequence comprising at least 296 amino acids, wherein the amino acid sequence and the amino acid sequence of SEQ ID NO:2, 4, 7, 9, 11, or 13 have at least 80%, 85%, 90%, or 95% identity based on the Clustal alignment method. The amino acid sequence preferably comprises the amino acid sequence of SEQ ID NO:2, 4, 7, 9, 11, or 13. The polypeptide preferably is a pantothenate synthetase.

In an eight embodiment, this invention relates to a method for isolating a polypeptide encoded by any of the polynucleotides of the first embodiment comprising transforming a cell with the polynucleotide, causing the polypeptide to be produced in the transformed cell, and isolating the polypeptide from the transformed cell.

In a ninth embodiment, the present invention relates to a virus, preferably a baculovirus, comprising any of the isolated polynucleotides of the present invention or any of the chimeric genes of the present invention.

In a tenth embodiment, the invention relates to a method of selecting an isolated polynucleotide that affects the level of expression of a pantothenate synthetase protein or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the pantothenate synthetase protein or enzyme activity in the host cell containing the isolated polynucleotide; and (d) comparing the level of the pantothenate synthetase protein or enzyme activity in the host cell containing the isolated polynucleotide with the level of the pantothenate synthetase protein or enzyme activity in the host cell that does not contain the isolated polynucleotide.

In an eleventh embodiment, the invention concerns a method of obtaining a nucleic acid fragment encoding a substantial portion of a pantothenate synthetase protein, preferably a plant pantothenate synthetase protein, comprising the steps of: synthesizing an oligonucleotide primer comprising a nucleotide sequence of at least one of 30 (preferably at least one of 40, most preferably at least one of 60) contiguous nucleotides derived from a nucleotide sequence selected from the group consisting of SEQ ID NO:1, 3, 5, 6, 8, 10, or 12, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a pantothenate synthetase protein amino acid sequence.

In a twelfth embodiment, this invention relates to a method of obtaining a nucleic acid fragment encoding all or a substantial portion of the amino acid sequence encoding a pantothenate synthetase protein comprising the steps of:

probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a thirteenth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the pantothenate synthetase polynucleotide in an amount sufficient to complement a null mutant to provide a positive selection means.

In a fourteenth embodiment, this invention relates to a method of altering the level of expression of a pantothenate synthetase protein in a host cell comprising: (a) transforming a host cell with a chimeric gene of the present invention; and (b) growing the transformed host cell under conditions that are suitable for expression of the chimeric gene wherein expression of the chimeric gene results in production of altered levels of the pantothenate synthetase protein in the transformed host cell.

A further embodiment of the instant invention is a method for evaluating at least one compound for its ability to inhibit the activity of a pantothenate synthetase, the method comprising the steps of: (a) transforming a host cell with a recombinant DNA construct of the invention; (b) growing the transformed host cell under conditions that are suitable for expression of the recombinant DNA construct wherein expression of the recombinant DNA construct results in production of a pantothenate synthetase; (c) optionally purifying the pantothenate synthetase expressed by the transformed host cell; (d) treating the pantothenate synthetase with a compound to be tested; and (e) comparing the activity of the pantothenate synthetase that has been treated with a test compound to the activity of an untreated pantothenate synthetase, thereby evaluating at least one compound for its ability to inhibit pantothenate synthetase activity.

BRIEF DESCRIPTION OF THE DRAWING AND SEQUENCE LISTINGS

The invention can be more fully understood from the following detailed description and the accompanying drawing and Sequence Listing which form a part of this application.

FIGS. 1A and 1B show a comparison of the amino acid sequences of pantothenate synthetases from corn (SEQ ID NOs:2 and 4), eucalyptus (SEQ ID NO:7), soybean (SEQ ID NO:9), tulip (SEQ ID NO:11), and wheat (SEQ ID NO:13) compared with the rice and lotus (SEQ ID NOs:14 and 15) sequences found in PCT application WO 99/42565 published Aug. 26, 1999. The sequences all start at the methionine codon believed to be the amino terminus of each protein (the amino-terminal extensions from wheat and eucalyptus have been removed for the alignment and in the estimation of percent identity found in Table 4).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

Two sequences with substantial homolgy to pantothenate synthase genes are found in corn, implying this enzyme as being encoded by a multigene family in plants. Multigene families have been notoriously difficult to manipulate through classical breeding approaches.

TABLE 1

Plant Pantothenate Synthetase/Pantoate-Beta-Alanine Ligase

| | | SEQ ID NO: | |
| --- | --- | --- | --- |
| Plant | Clone Designation | (Nucleotide) | (Amino Acid) |
| maize [Zea mays] | cpj1c.pk005.c12:fis | 1 | 2 |
| maize [Zea mays] | cr1n.pk0125.c12:fis | 3 | 4 |
| eucalyptus [Eucalyptus grandis] | eej1c.pk005.p14:fis | 6 | 7 |
| soybean [Glycine max] | ssl.pk0021.d7:fis | 8 | 9 |
| tulip [Tulipa fosteriana] | etb1c.pk004.j20:fis | 10 | 11 |
| wheat [Triticum aestivum] | wlm96.pk036.k8:fis | 12 | 13 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822. The clone eej1c.pk005.p14:fis (SEQ ID NO:5) was found to be an unspliced variant. Removal of the intron sequence (703–1163, with classic GT . . . AG border sequences) yields the eucalyptus coding sequence (SEQ ID NO:6) and its translation product (SEQ ID NO:7). The eucalyptus and wheat proteins have amino-terminal extensions of 37 (RPACILLLALPKFLLLSLSHPIPRNSLLSNPFRCPPP) and 12 amino acids (SSDQFDCSAPDP), respectively. Also, the first 29 nucleotides of the wheat sequence appears to be vector sequence (this is is not included in the 12 amino acid extension or in the wheat coding region).

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 30 contiguous nucleotides, preferably at least one of 40 contiguous nucleotides, most preferably one of at least 60 contiguous nucleotides derived from SEQ ID NOs:1, 3, 5, 6, 8, 10, and 12, or the complement of such sequences.

The term "isolated" polynucleotide refers to a polynucleotide that is substantially free from other nucleic acid sequences, such as and not limited to other chromosomal and extrachromosomal DNA and RNA, that normally accompany or interact with it as found in its naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 30 (preferably at least one of 40, most preferably at least one of 60) contiguous nucleotides derived from a nucleotide sequence selected from the group consisting of SEQ ID NOs:1, 3, 5, 6, 8, 10, and 12, and the complement of such nucleotide sequences may be used in methods of selecting an isolated polynucleotide that affects the expression of a pantothenate synthetase polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The CDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) first nucleotide sequence encoding a polypeptide of at least 296 amino acids having at least 80%, 85%, 90%, 95%, or 100% identity based on the Clustal method of alignment when compared to a polypeptide selected from the group consisting of SEQ ID NOs:2, 4, 7, 9, 11, and 13, or (b) a second nucleotide sequence comprising the complement of the first nucleotide sequence.

Preferably, the first nucleotide sequence comprises a nucleic acid sequence selected from the group consisting of SEQ ID NOs:1, 3, 5, 6, 8, 10, and 12, that codes for the polypeptide selected from the group consisting of SEQ ID NOs:2, 4, 7, 9, 11, and 13.

Nucleic acid fragments encoding at least a portion of several pantothenate synthetases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other pantothenate synthetase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID. NOs:1, 3, 5, 6, 8, 10, and 12 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a pantothenate synthetase polypeptide, preferably a substantial portion of a plant pantothenate synthetase polypeptide, comprising the steps of: synthesizing an oligonucleotide primer comprising a nucleotide sequence of at least one of 30 (preferably at least one of 40, most preferably at least one of 60) contiguous nucleotides derived from a nucleotide sequence selected from the group consisting of SEQ ID NOs:1, 3, 5, 6, 8, 10, and 12, and the complement of such nucleotide sequences; and amplifying a nucleic acid fragment (preferably a cDNA inserted in a cloning vector) using the oligonucleotide primer. The amplified nucleic acid fragment preferably will encode a portion of a pantothenate synthetase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of coenzyme A in those cells. Reductions in the level of coenzyme A are deleterious to growth and viability. Cloning and expression of pantothenate synthetase chimeric genes allows for the screening of chemicals that specifically inhibit pantothenate synthetase and therefore have herbicidal properties. Since most mammals do not possess pantothenate synthetase activities, herbicides targeting this enzyme should be relatively benign to animals. Furthermore, plants engineered to overexpress pantothenate synthetase, or expressing a mutated form of pantothenate synthetase that is resistant to the herbicide, would have agronomic value. Treating fields with herbicides inhibiting pantothenate synthetase would kill undesirable plants, while allowing the resistant plants to grow.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 296 amino acids that has at least 85% identity based on the Clustal method of alignment when compared to a polypeptide selected from the group consisting of SEQ ID NOs:2, 4, 7, 9, 11, and 13.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded pantothenate synthetases. An example of a vector for high level expression of the instant polypeptides in a bacterial host is provided (Example 6).

Additionally, the instant polypeptides can be used as a target to facilitate design and/or identification of inhibitors of those enzymes that may be useful as herbicides. This is desirable because the polypeptides described herein catalyze various steps in coenzyme A synthesis, namely the formation of pantothenate. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Composition of cDNA Libraries; Isolation and Sequencing of cDNA Clones cDNA libraries representing mRNAs from various corn, eucalyptus, soybean, tulip, and wheat tissues were prepared. The characteristics of the libraries are described below.

TABLE 2 cDNA Libraries from Corn, Eucalyptus, Soybean, Tulip, and Wheat

| Library | Tissue | Clone |
|---|---|---|
| cpj1c | Corn (*Zea mays* L.) pooled BMS treated with chemicals related to membrane ionic force | cpj1c.pk005.c12:fis |
| cr1n | Corn Root From 7 Day Old Seedling* | cr1n.pk0125.c12:fis |
| eej1c | Eucaplyptus grandis juevenile leaves | eej1c.pk005.p14:fis |
| ssl | Soybean Seedling 5–10 Days After Germination | ssl.pk0021.d7:fis |
| etb1c | Tulip (*Tulipa fosteriana*, Yellow Emperor) developing bulbs (10 day post petal drop) | etb1c.pk004.j20:fis |
| wlm96 | Wheat Seedlings 96 Hours After Inoculation With *Erysiphe graminis* f. sp tritici | wlm96.pk036.k8:fis |

*This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding pantothenate synthetases were identified by conducting BLAST (Basic Local Alignment Search Tool; Altschul et al. (1993) *J. Mol. Biol.* 215:403–410; see also the explanation of the BLAST algorithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Pantothenate Synthetase

The BLASTX search using the EST sequences from clones listed in Table 3 revealed similarity of the polypeptides encoded by the cDNAs to pantothenate synthetase from rice (*Oryza sativa*) (NCBI Accession No. gi 2292978) or lotus (*Lotus japonicus*) (NCBI Accession No. gi 2292921). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to Pantothenate Synthetase

| Clone | Status | BLAST pLog Score 2292978 | BLAST pLog Score 2292921 |
|---|---|---|---|
| cpj1cpk005.c12 | EST | 132.00 | — |
| cr1n.pk0125.c12 | EST | 131.00 | — |
| eej1c.pk005.p14 | EST | — | 124.00 |
| ss1.pk0021.d7 | EST | — | 142.00 |
| etb1c.pk004.j20 | EST | — | 93.22 |
| wlm96.pk036.k8 | EST | 128.00 | — |

FIG. 1 presents an alignment of the amino acid sequences set forth in SEQ ID NOs:2, 4, 7, 9, 11, and 13, and the rice and lotus (SEQ ID NOs:14 and 15) sequences found in PCT application WO 99/42565 published Aug. 26, 1999. The sequences all start at the methionine codon believed to be the amino terminus of each protein (the amino-terminal extensions from wheat and eucalyptus are not part of the alignment or in the estimation of percent identity found in Table 4).

The data in Table 4 represents a calculation of the percent identity of the amino acid sequences set forth in SEQ ID NOs:2, 4, 7, 9, 11, and 13 and the rice and lotus sequences.

TABLE 4

Percent Identity of Amino Acid Sequences
Deduced From the Nucleotide Sequences of
CDNA Clones Encoding Polypeptides
Homologous to Pantothenate Synthetase

| SEQ ID NO. | Percent Identity to 2292978 | Percent Identity to 2292921 |
|---|---|---|
| 2 | 74.4 | 58.1 |
| 4 | 74.1 | 58.1 |
| 7 | 57.2 | 68.8 |
| 9 | 54.8 | 78.6 |
| 11 | 56.4 | 56.8 |
| 13 | 72.5 | 58.4 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a pantothenate synthetase. These sequences represent the first dicot, corn, soybean, eucalyptus, tulip, and wheat sequences encoding pantothenate synthetase known to Applicant.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (Ncol or Smal) can be incorporated into the oligonucleotides to provide proper orientation of the DNA fragment when inserted into the digested vector pML103 as described below. Amplification is then performed in a standard PCR. The amplified DNA is then digested with restriction enzymes Ncol and Smal and fractionated on an agarose gel. The appropriate band can be isolated from the gel and combined with a 4.9 kb NcoI-Smal fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit Pantothenate Synthetase Activity The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for pantothenate synthetase are presented by Genschel et al. (1999) *Biochem J* 341:669–678 or in PCT application WO 99/42565 published Aug. 26, 1999.

It is well known that many plant genes can complement null mutations in homologous yeast genes (Rossi et al. (1998) *Mol Gen Genet* 258:288–96; Gachotte et al (1996) *Plant J* 9:391–8; Bednarek et al. (1994) *Plant Physiol* 104:591–6). The yeast null mutation in the pantothenate synthetase gene is an auxotroph for pantothenate. A null mutant yeast can be complemented with any of the pantothenate synthetase genes of the present invention, under the control of the appropriate regulatory sequences, thereby releasing pantothenate auxotrophy. These yeast cells can then be used to screen compounds that inhibit the complementing plant pantothenate synthetase enzyme, by screening for non-growth on minimal media but growth on minimal media supplemented with pantothenate.

What is claimed:

1. An isolated polynucleotide comprising:
   (a) a nucleotide sequence encoding a polypeptide having pantothenate synthetase activity, wherein the amino acid sequence of the polypeptide and the amino acid sequence of SEQ ID NO:9 have at least 90% sequence identity based on the Clustal alignment method, or
   (b) the complement of the nucleotide sequence, wherein the complement and the nucleotide sequence contain the same number of nucleotides and are 100% complementary.

2. The polynucleotide of claim 1, wherein the amino acid sequence of the polypeptide and the amino acid sequence of SEQ ID NO: 9 have at least 95% sequence identity based on the Clustal alignment method.

3. The polynucleotide of claim 1, wherein the polypeptide comprises the amino acid sequence of SEQ ID NO:9.

4. The polynucleotide of claim 1, wherein the nucleotide sequence comprises the nucleotide sequence of SEQ ID NO:8.

5. A vector comprising the polynucleotide of claim 1.

6. A recombinant DNA construct comprising the polynucleotide of claim 1 operably linked to a regulatory sequence.

7. A method for transforming a cell comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *

UNITED STATES PATENT AND TRADEMARK OFFICE
CERTIFICATE OF CORRECTION

PATENT NO. : 6,881,878 B2 Page 1 of 1
APPLICATION NO. : 10/033269
DATED : April 19, 2005
INVENTOR(S) : Steven Gutteridge et al.

It is certified that error appears in the above-identified patent and that said Letters Patent is hereby corrected as shown below:

Please delete item [76], Leslie T. Harvell and Emil M. Orozco as co inventors.

Signed and Sealed this

Fifth Day of December, 2006

JON W. DUDAS
*Director of the United States Patent and Trademark Office*